(12) United States Patent  (10) Patent No.: US 9,192,546 B2
Zickerman et al.  (45) Date of Patent: Nov. 24, 2015

(54) SUNSCREEN SHEET

(71) Applicants: Terry Zickerman, Montclair, NJ (US);
Stephen Liaci, West Orange, NJ (US)

(72) Inventors: Terry Zickerman, Montclair, NJ (US);
Stephen Liaci, West Orange, NJ (US)

( * ) Notice: Subject to any disclaimer, the term of this patent is extended or adjusted under 35 U.S.C. 154(b) by 126 days.

(21) Appl. No.: 13/971,030

(22) Filed: Aug. 20, 2013

(65) Prior Publication Data

US 2014/0072606 A1  Mar. 13, 2014

Related U.S. Application Data

(60) Provisional application No. 61/698,099, filed on Sep. 7, 2012.

(51) Int. Cl.
*A61K 8/02* (2006.01)
*A61Q 17/04* (2006.01)

(52) U.S. Cl.
CPC .............. *A61K 8/0208* (2013.01); *A61Q 17/04* (2013.01)

(58) Field of Classification Search
None
See application file for complete search history.

(56) References Cited

U.S. PATENT DOCUMENTS

| | | | |
|---|---|---|---|
| 3,864,473 A | 2/1975 | Ciaudelli | |
| 4,550,035 A | 10/1985 | Smith | |
| 4,759,652 A | 7/1988 | Ulrich | |
| 5,017,365 A * | 5/1991 | Niedbala | 424/59 |
| 5,072,467 A | 12/1991 | Hunt | |
| 5,620,694 A | 4/1997 | Girardot | |
| 5,972,360 A | 10/1999 | Braun | |
| 6,054,120 A | 4/2000 | Burgoyne et al. | |
| 6,267,975 B1 * | 7/2001 | Smith et al. | 424/401 |
| 6,491,928 B1 * | 12/2002 | Smith, III | 424/401 |
| 7,144,570 B2 | 12/2006 | Gall et al. | |
| 7,198,780 B2 | 4/2007 | Dicianna | |
| 7,384,916 B2 | 6/2008 | Patt | |
| 7,467,420 B2 | 12/2008 | Ponce et al. | |
| 7,592,019 B2 | 9/2009 | Drucks et al. | |
| 8,012,495 B2 | 9/2011 | Luu et al. | |

(Continued)

FOREIGN PATENT DOCUMENTS

| | | |
|---|---|---|
| JP | 2001-058153 | 3/2001 |
| JP | 2005-211425 | 8/2005 |

(Continued)

OTHER PUBLICATIONS

Notification of Transmittal of the International Search Report and the Written Opinion of the International Searching Authority—Nov. 26, 2013.

*Primary Examiner* — Ernst V Arnold
*Assistant Examiner* — Jianfeng Song
(74) *Attorney, Agent, or Firm* — Tyson B. Benson; Advent, LLP

(57) ABSTRACT

The present disclosure relates to a cosmetic or dermatological sheet impregnated with a sunscreen fluid cosmetic composition. Specifically, the present disclosure relates to a cosmetic or dermatological sheet impregnated with a sunscreen fluid cosmetic composition and method to apply sunscreen to the human user's back or entire body. The sheet may have stitching and other composition or structural aspects to increase the structural integrity, hand slits, mitts or finger holes in the fabric, and/or areas that are not impregnated with a sunscreen composition to enable the user to more easily or tightly grasp the sheet during application of the sunscreen composition. Additionally, the sheet may be used to apply sunscreen to the user's back or entire body more than once before discarding the sheet and may include or consist of dyes, paints, tints or emboss to change the color or design of the sheet.

20 Claims, 18 Drawing Sheets

(56) References Cited

U.S. PATENT DOCUMENTS

| | | |
|---|---|---|
| 2002/0071859 A1 | 6/2002 | Gott et al. |
| 2002/0187181 A1* | 12/2002 | Godbey et al. ................ 424/443 |
| 2003/0012809 A1 | 1/2003 | Gott et al. |
| 2003/0206940 A1* | 11/2003 | Gott et al. .................... 424/443 |
| 2005/0048856 A1* | 3/2005 | Hauser et al. .................. 442/59 |
| 2005/0063924 A1 | 3/2005 | Maniscalco |
| 2006/0019571 A1 | 1/2006 | Lange et al. |
| 2006/0110419 A1 | 5/2006 | Keilman et al. |
| 2011/0262209 A1 | 10/2011 | Landy |

FOREIGN PATENT DOCUMENTS

| | | | |
|---|---|---|---|
| JP | 2007-224015 | | 9/2007 |
| KR | 10-2008-0096903 | | 11/2008 |
| KR | 10-2009-0021658 | | 3/2009 |
| WO | WO-2010076731 | * | 7/2010 |

* cited by examiner

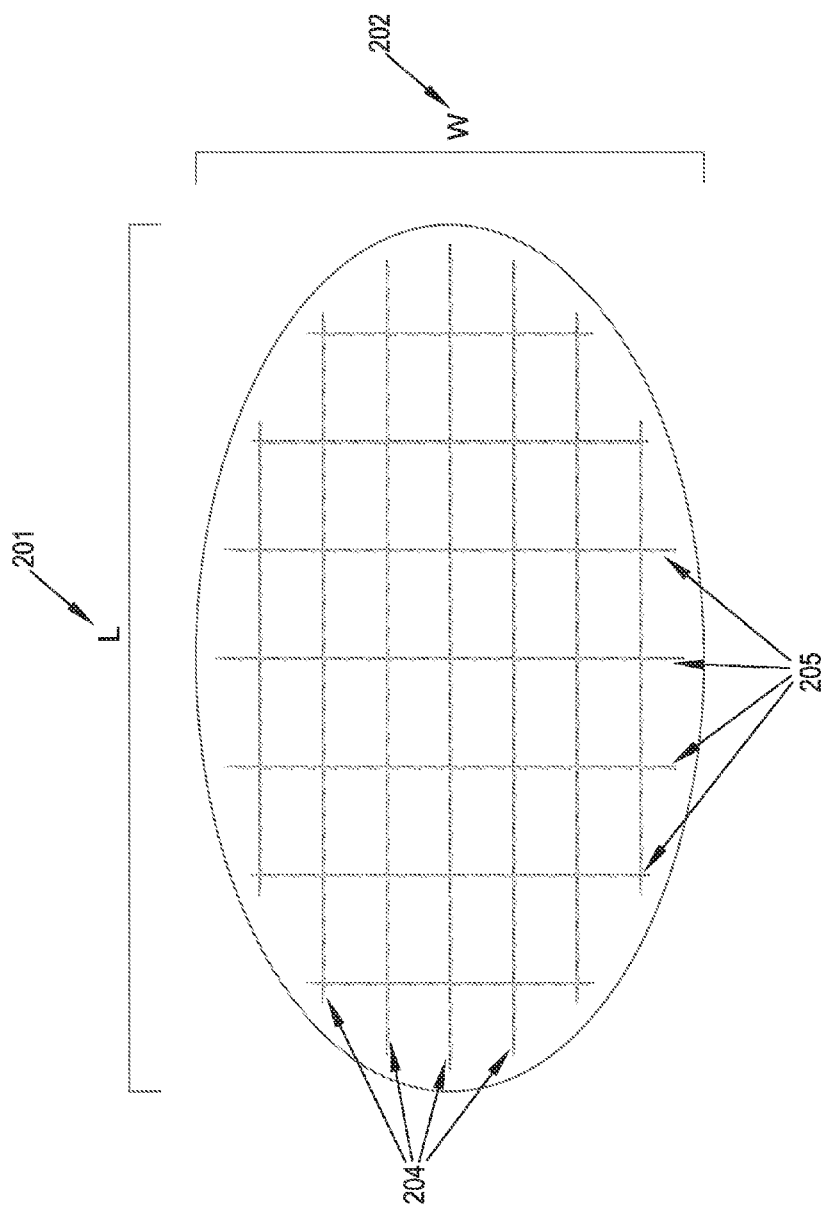

SUNSCREEN SHEET

BACKGROUND

It is well known that exposure to the sun's ultraviolet radiation can cause a myriad of health problems, ranging from simple sunburns to severely malignant forms of cancer, such as melanoma. It is also well known that the application of a sunscreen composition to the skin can significantly reduce the effects of the sun's UV radiation.

Sunscreen compositions have been in use for decades and have been formulated to block the sun's UV photons. Organic chemical molecules such as para-aminobenzoic acid (PABA) contain conjugated pi systems and are therefore able to absorb UV photons, effectively blocking the UV radiation. Inorganic particulates such as zinc oxide block UV radiation by reflecting or scattering the UV photons. However, the size of the inorganic particulate must be matched to the wavelength of the UV radiation for proper effect. In addition to organic chemical molecules and inorganic particulates, a newer class of molecules, organic particulates such as Tinosorb M, are being used in sunscreen compositions. Organic particulates block UV radiation by absorbing and reflecting the UV photons. Like the inorganic particulates, the size of the organic particulate must be matched to the wavelength of the UV radiation for proper effect.

A particular sunscreens ability to block the sun's UV radiation can be quantified by the sun protection factor (SPF), an integer number typically ranging from about 2 to about 100. The higher the SPF integer, the greater the ability to block UV radiation, although the claimed increase in effectiveness of compounds having SPF numbers higher than about 50 is being questioned. The SPF is dependent on both the composition of the sunscreen and the amount applied to a given area. The SPF of a specific sunscreen is based on the uniform application of about 2 mg of sunscreen to a square centimeter of exposed skin (i.e., about 2 mg/cm$^2$). The exposed surface area of an average adult human's back is approximately 3,114 cm$^2$ and the exposed surface area of an adult human's entire body is approximately 16,300 cm$^2$, requiring about 6.2 grams and about 32.6 grams of sunscreen to meet the SPF requirements, respectively. See Table 1, adapted from *A simple measure for applying sunscreen while on holidays, Dermatology Journal Online*, Vol. 3, No. 9; this reference is incorporated herein by reference in its entirety.

TABLE 1

Exposed Surface Area of Average Adult Human Body

| Segment | Percentage | Surface (cm$^2$) | Recommended Dosage (mg) |
| --- | --- | --- | --- |
| Face, neck | <9% | 685 | 1,370 |
| Upper limb (right) | 9% | 1,557 | 3,114 |
| Upper limb (left) | 9% | 1,557 | 3,114 |
| Back | 18% | 3,114 | 6,228 |
| Torso | 18% | 3,114 | 6,228 |
| Lower limb (right) | 18% | 3,114 | 6,228 |
| Lower limb (left) | 18% | 3,114 | 6,228 |

Typically, sunscreen is formulated as a gel or lotion, although aerosol sprays have lately been added to the market. Regardless of the formulation, an even distribution of the sunscreen on the user's skin is required for effective protection from the sun's UV radiation. Gel and lotion formulations are often viscous and difficult to apply evenly over the skin, resulting in areas saturated with sunscreen and other areas which are under-treated and prone to UV damage. Certainly the presence of body hair commonly found on the chests, backs and legs of adult makes the even application of viscous gel and lotion formulations less likely. In an attempt to help aid the thorough and even application of sunscreen, aerosol sprays were developed. Instead of rubbing viscous lotions over their skin, users were able to simply spray the sunscreen on their exposed skin. However, environmental factors such as rain or wind can affect the distribution. In addition, aerosol sprays can be difficult to use to reach all areas of the human body, such as the back, and users are sometimes hesitant to use aerosol sprays around sensitive areas such as the eyes and mouth. In addition, liquids, aerosol sprays, gels and lotions are typically not allowed aboard an aircraft due to security restrictions and regulations.

Another drawback of gels, lotions, aerosol sprays and even towelettes impregnated with sunscreen compositions is that the user is not able to adequately apply a thorough and even coating to their body, especially their back, without the assistance of someone else.

In addition to this size constraint, the towelettes are usually fragile when impregnated with sunscreen, so tearing can easily occur. Finally, the towelettes are a one-time use product and are to be discarded after only one application of sunscreen, usually to the human face.

SUMMARY

In view of the above, it would be advantageous to have a sheet impregnated with a sunscreen composition to facilitate uniform application of the sunscreen over the human user's back or entire exposed skin. Accordingly, the size and shape of the sheet will be constructed as to allow the human user to apply an even application of sunscreen over their back or entire body with or without assistance from another person. As such, the sunscreen formulation and sheet composition will be matched to ensure adequate uptake and retention of the sunscreen while allowing an even distribution caused by rubbing the sheet over the user's skin. Stitching or other structural features of the sheet may be utilized to increase the shear and tensile strength to prevent tearing during the application of sunscreen. Additionally, hand slits or "mitts" may be incorporated into the edges of the sheet or areas that are not impregnated with a sunscreen composition may be included to help the user hold the sheet during sunscreen application. The sheet and sunscreen product can also be created to allow more than one application of sunscreen to the user's back or entire exposed skin.

Accordingly, the present disclosure comprises a cosmetic or dermatological sheet which includes a water-insoluble sheet and a sunscreen fluid cosmetic composition impregnated into the sheet.

While the sheet may be formed to common geometric shapes such as rectangles, ovals or hourglasses, other geometric shapes of the present disclosure are contemplated. Other geometric shapes may be selected from the following group consisting of oval, elliptical, racetrack oval, surfboard, egg, triangle, star, square, pentagon, hexagon, heptagon, octagon, heart, diamond, crescent, moon, trapezoid, rhombus, kite, trapezium, marquise, pear, emerald, cushion, baguette, flag, single arrow, double arrow, shamrock, paisley, boat, kidney, demi lune, clipped corners square or rectangles, serpentine, cross, moon, butterfly, parallelogram, vector shapes, organic shapes and other geometric shapes.

According to another aspect of the disclosure, the sheet is designed to absorb and retain the sunscreen formulation and has a surface area greater than about 80 square inches. In another embodiment, each side of a sheet which is designed to absorb and retain the sunscreen formulation has a surface area greater than about 80 square inches.

In certain embodiments, the length to width ratio of the sheet is greater than about 1.6. In an example embodiment, the length of the sheet is in the range of about 12 inches to about 100 inches in length and in the range of about 5 inches to about 24 inches in width, more preferably in the range of about 24 inches to about 72 inches in length and in the range of about 6 inches to about 12 inches in width.

Additionally, in certain embodiments, the sheet is greater than about 10 inches in length and about 8 inches in width.

According to another aspect of the disclosure, the sheet is capable of dispensing enough of the sunscreen fluid cosmetic composition to cover the exposed skin of an adult or other human's back or entire body.

In certain embodiments the sheet may have hand slits, mitts or finger holes, enabling the user to insert their fingers or hands, incorporated along the border of the sheet, or may include an area or areas that are not impregnated with a sunscreen composition for holding the sheet during sunscreen application.

In another aspect of the disclosure, the sheet may incorporate horizontal and/or vertical stitching into the sheet. Additionally, in some example embodiments, a plastic, rubber or resin structural sheet may be fused to the back of a sheet impregnated with the sunscreen fluid cosmetic composition or may be incorporated between two sheets impregnated with the sunscreen fluid cosmetic composition. Optionally, thermal or chemical binders may be incorporated into the fabric of the sheet. Each of these embodiments is meant to increase the mechanical strength of the sheet(s) impregnated with the sunscreen fluid cosmetic composition.

According to another aspect of the disclosure, the sheet may comprise a granulated, textured or quilted surface to increase the amount of sunscreen fluid cosmetic composition retained by the sheet. The sheet may also include or consist of dyes, paints, tints or emboss to change the color or design of the sheet.

In another example embodiment, the sheet impregnated with the sunscreen fluid cosmetic composition is reusable and thus capable of applying at least one coating of sunscreen to the user's back or entire body.

In the example embodiment, the sheet is capable of dispensing an even application of sunscreen over the user's back or entire body with or without assistance from another person The above, and other features and advantages of the present disclosure will become apparent from the following description read in conjunction with the accompanying drawings, in which like reference numerals designate the same elements.

BRIEF DESCRIPTION OF THE DRAWINGS

The novel features of this disclosure, as well as the disclosure itself, both as to its structure and its operation, will be best understood from the accompanying drawings, taken in conjunction with the accompanying description, in which similar reference characters refer to similar parts and in which:

FIGS. 2B, 2C, 2D and 2E depict top-down views of various embodiments in an oval sheet.

DETAILED DESCRIPTION

Figure 1A:
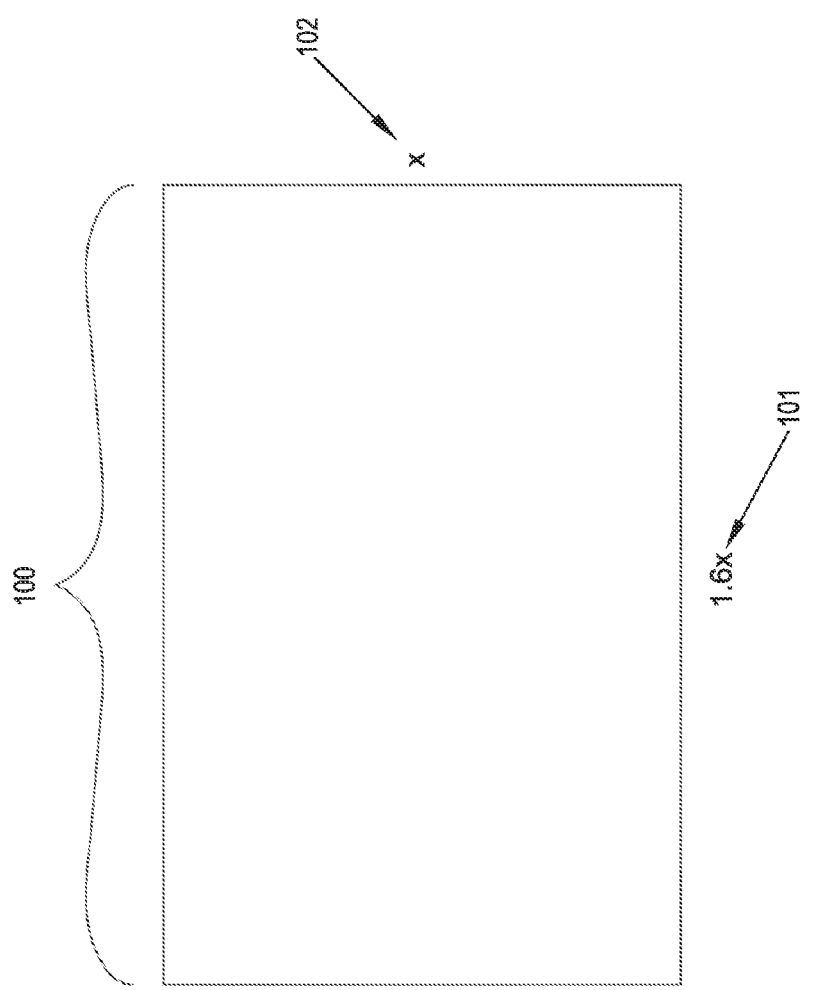
FIG. 1A depicts a top-down view of a rectangular sheet.
Figure 1B:
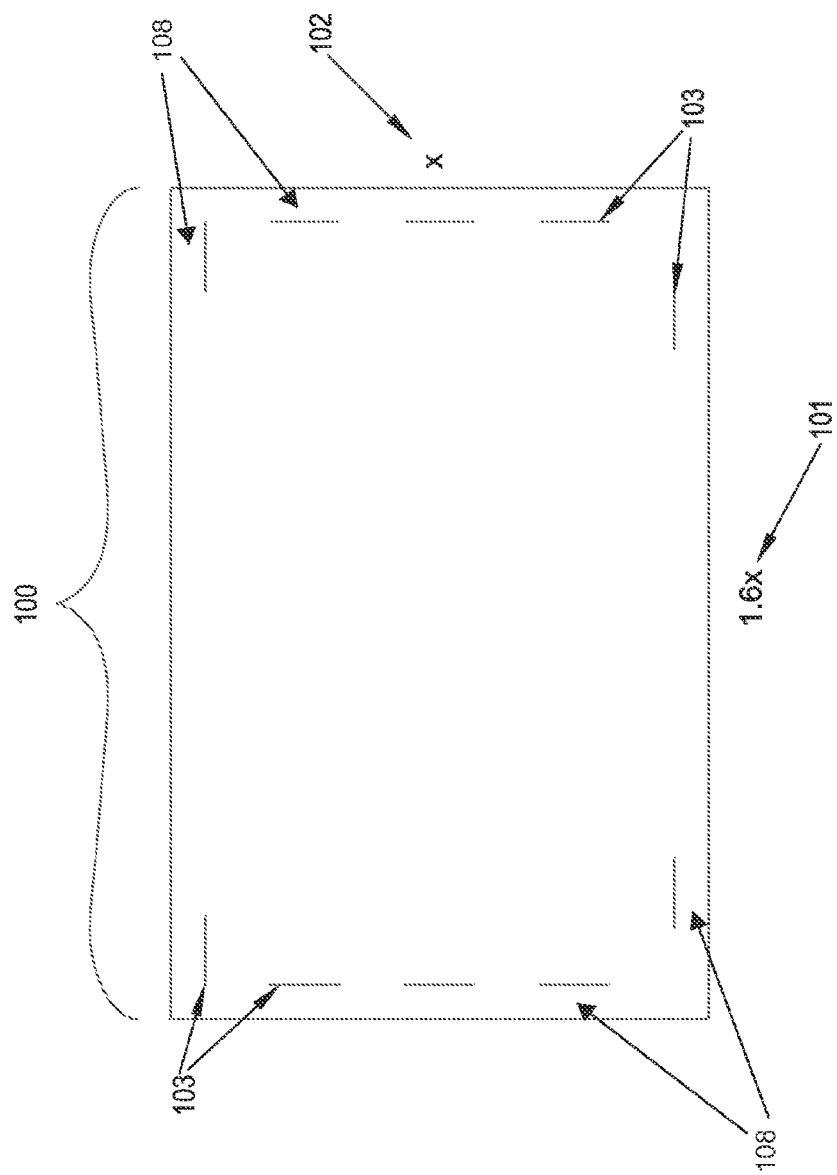
FIGS. 1B, 1C, 1D and 1E depict top-down views of various embodiments in a rectangular sheet.
Figure 1C:
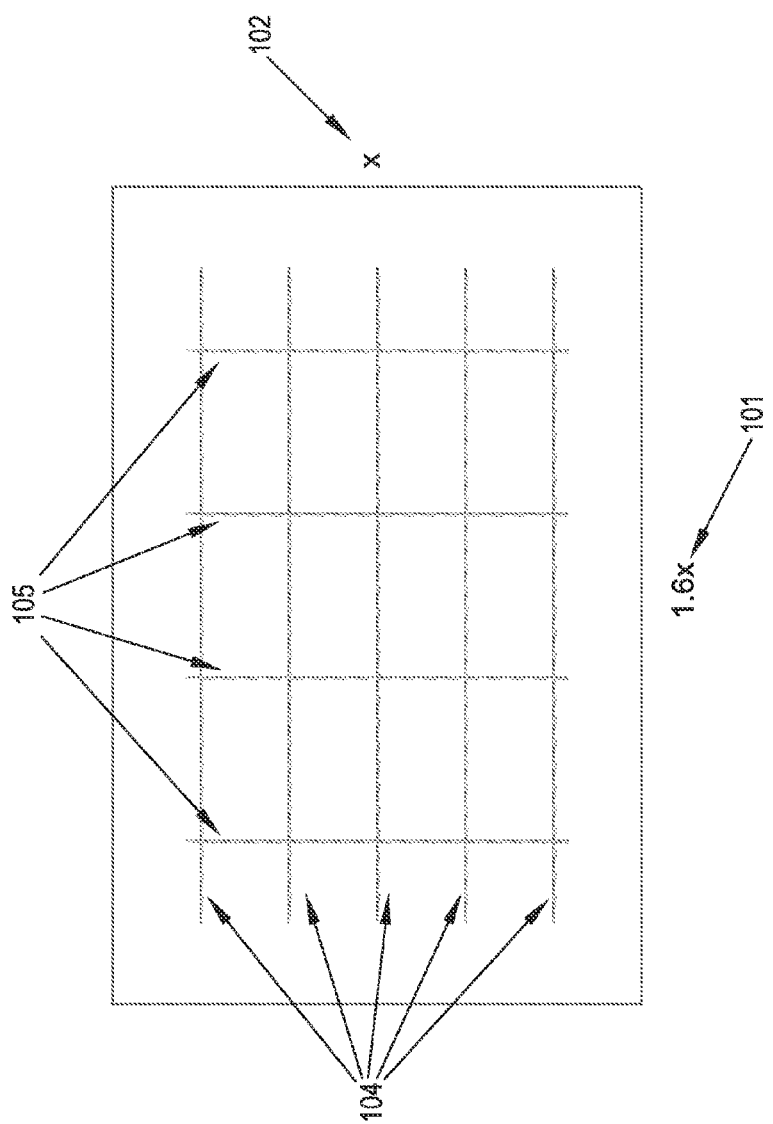
Figure 1D:
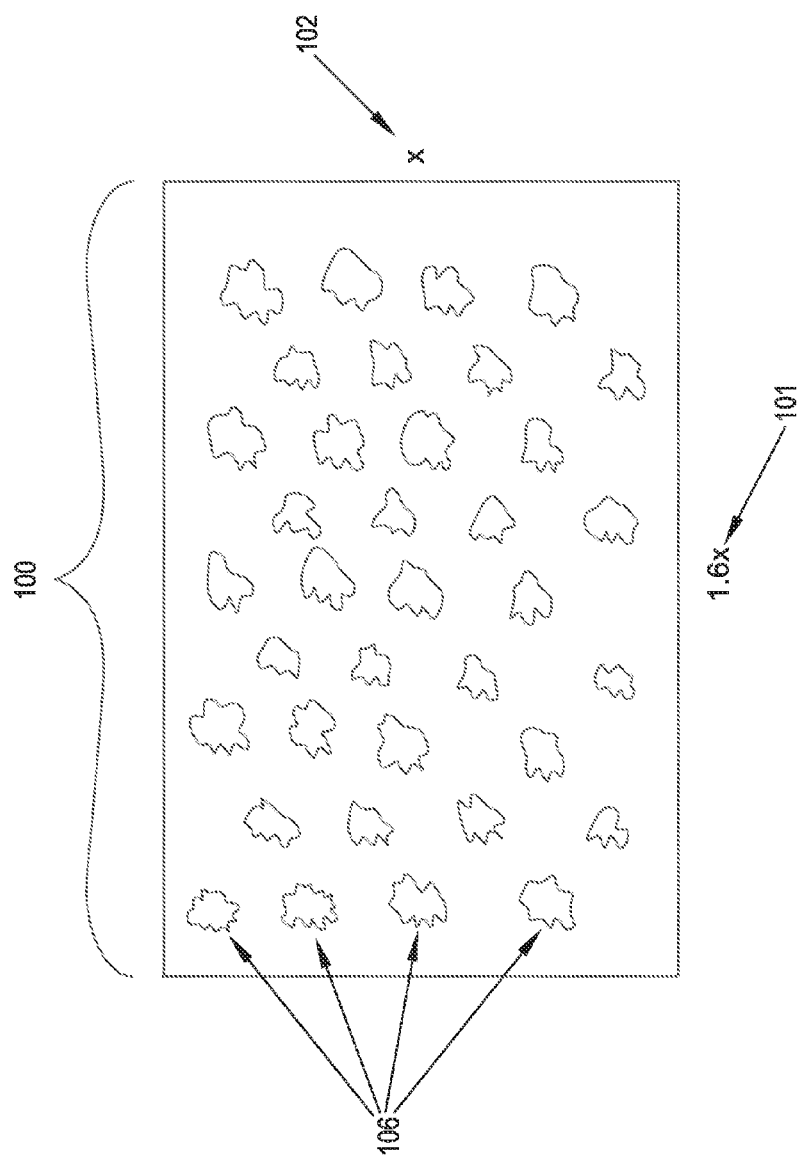

Reference will now be made in detail to several embodiments of the disclosure that are illustrated in the accompanying drawings. Wherever possible, same or similar reference numerals are used in the drawings and the description to refer to the same or like parts or steps. The drawings are in simplified form and are not to precise scale. For purposes of convenience and clarity only, directional terms, such as top, bottom, up, down, over, above, and below may be used with respect to the drawings. These and similar directional terms should not be construed to limit the scope of the disclosure in any manner.

The sheet of this disclosure is to be made of a composition which has the following characteristics: insoluble in water, flexible and easily formed into a sheet or towel of many different shapes and sizes, capable of absorbing and retaining the sunscreen composition, unreactive with the components of the sunscreen composition, capable of releasing the sunscreen composition when the user rubs the sheet on their skin and having a high shear and tensile strength.

Insoluble sheets are those which do not dissolve or break apart upon immersion in water. Low viscosity sunscreen compositions formulated to be impregnated into a sheet are often aqueous based. In addition, since the sunscreen may be applied to a wet body, insolubility in water is a desirable feature.

Flexible sheets can be formed from woven or non-woven fibrous materials or a mixture thereof. Non-woven sheets may be preferred for economic reasons. Non-woven sheets are made from individual fibers which are not joined together by a weaving process. Instead, the individual fibers are compacted into a sheet or web structure and bonded together using a chemical, mechanical or thermal process. The fibers can be randomly oriented or carded into a specific orientation. Although non-woven sheets are preferred for economic reasons, the generally lack the strength of a woven sheet and therefore are susceptible to structural damage such as tearing or ripping.

Woven or non-woven fibrous materials can be either natural or synthetic. Natural fibers are those which are derived from natural sources such as animal, insect or plant. Natural fibers can generally be categorized as being either silk, keratin based or cellulose based. Synthetic fibers are those which are man-made or originally derived from natural sources and then chemically modified.

Non-limiting examples of keratin based natural fibers useful in the present disclosure are those selected from the group consisting of alpaca hair fibers, camel hair fibers, goat hair fibers, horse hair fibers, wool fibers and other animal hair fibers. Non-limiting examples of cellulose based natural fibers useful in the present disclosure are those selected from the group consisting of cotton fibers, flax fibers, hemp fibers, jute fibers, linen fibers, ramie fibers, sisal fibers and wood pulp.

Non-limiting examples of synthetic fibers useful in the present disclosure are those selected from the group consisting of acetate fibers, acrylic fibers, cellulose ester fibers, modacrylic fibers, polyamide fibers such as nylon fibers and aramid fibers, polyester fibers, polyolefin fibers such as polyethylene fibers and polypropylene fibers, polyethylene terephthalate fibers (PET), polyurethane fibers and foams, polyvinyl chloride fibers and rayon fibers, hydroentangeled rayon composition, spandex fibers, lycra fibers, neoprene fibers and elastane fibers.

Whether the sheet is woven or non-woven, it can be processed to generate a wide variety of shapes and forms. Non-limiting examples of sheet shapes useful in the present disclosure are those selected from the group consisting of oval, elliptical oval, racetrack oval, rectangle, surfboard, hourglass, egg, triangle, star, square, pentagon, hexagon, heptagon, octagon, heart, diamond, crescent, trapezoid, rhombus, kite, trapezium, marquise, pear, emerald, cushion, baguette, flag, single arrow, double arrow, shamrock, paisley, boat, kidney, demilune, clipped corners square or rectangles, serpentine, cross, moon, butterfly, parallelogram, inverted and tapered hourglass, tapered cylinder, double candlestick, vector shapes, and/or organic shapes.

Sheets may be sized to hold enough sunscreen to cover the entire exposed skin of a variety of body shapes and sizes, including from a small child to a large adult human, or may be sized for only a specific body part such as the back, as shown in Table 1. Although the ranges shown in Table 1 are for the average adult human, one of ordinary skill in the art will recognize the need to adjust the ranges of sunscreen held by individual sheets based on the changes in body size dictated by, for example, age, weight, height, or body mass.

Sheets may also consist of a single or multiple areas that are not impregnated with a sunscreen composition to allow, for example, for holding the sheet during sunscreen application. To accomplish this, the sheet may have a plastic, resin, film or some other material to separate the impregnated area(s) of the sheet versus the non-impregnated area(s) of the sheet.

Sheets may also include or consist of dyes, paints, tints or emboss to change the color or design of the sheet. Such color or design may be in the form of advertising, decorations, logos, trademarks, company names, images, useful information and the like.

Illustrative and non-limiting examples of three different sheet shapes are depicted in FIGS. 1, 2 and 3. Rectangular sheet 100 in FIG. 1A has elements 101 and 102 showing the length and width dimensions of the sheet, respectively. In the example embodiment, the length/width ratio will be greater than about 1.6. In an example embodiment, the length of the sheet is in the range of about 12 inches to about 100 inches in length and in the range of about 5 inches to about 24 inches in width, more preferably in the range of about 24 inches to about 72 inches in length and in the range of about 6 inches to about 12 inches in width. In addition, the surface area of the sheet designed to absorb and retain the sunscreen formulation will be greater than about 80 square inches. In another embodiment of the present disclosure, each side of the sheet designed to absorb and retain the sunscreen formulation will be greater than about 80 square inches.

Figure 2A:
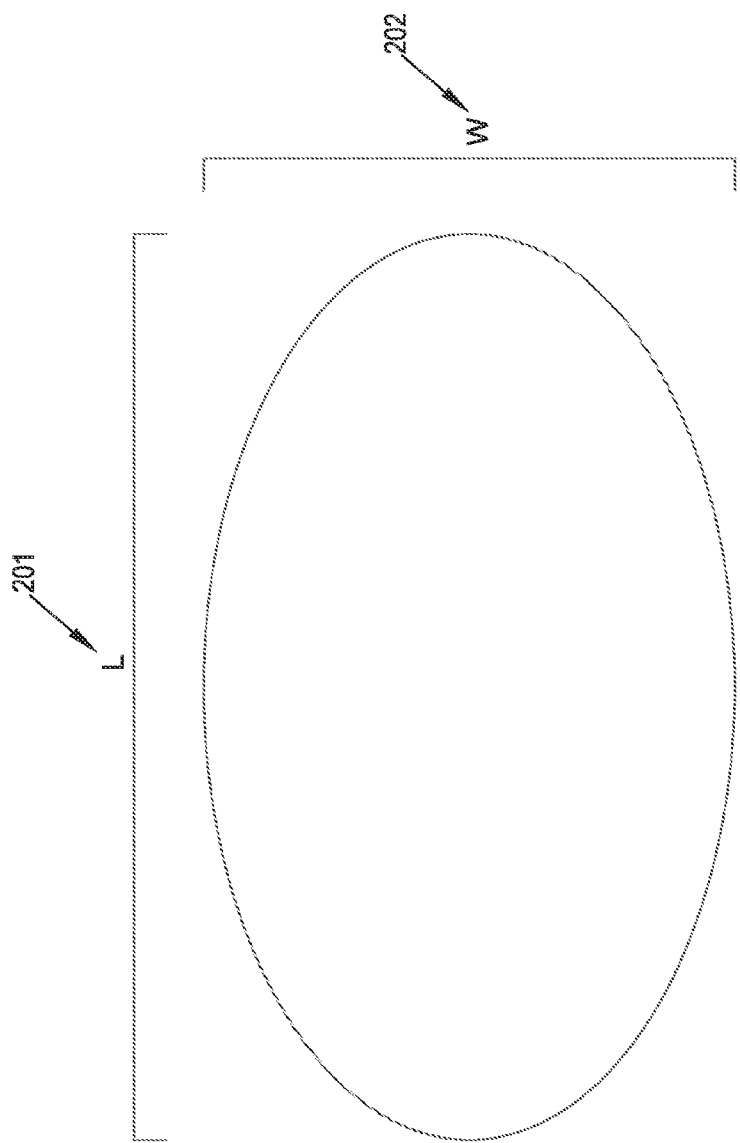
FIG. 2A depicts a top-down view of an oval sheet.
Figure 2B:
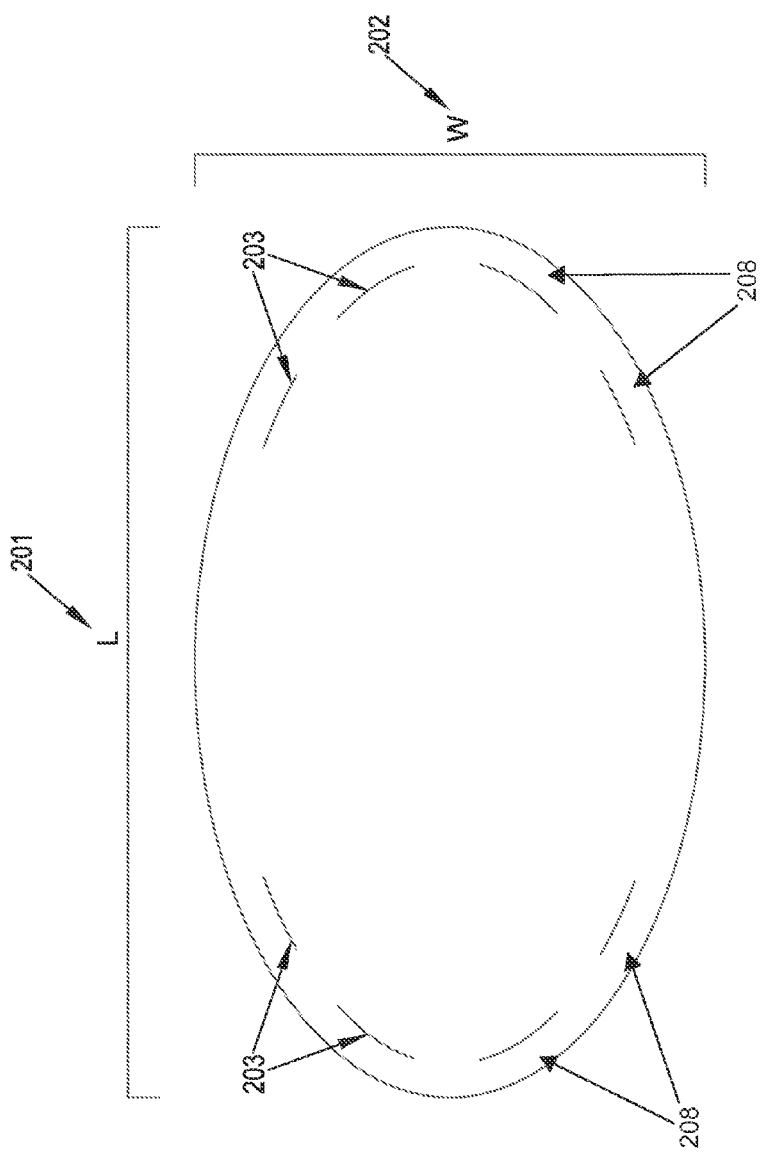
Figure 2D:
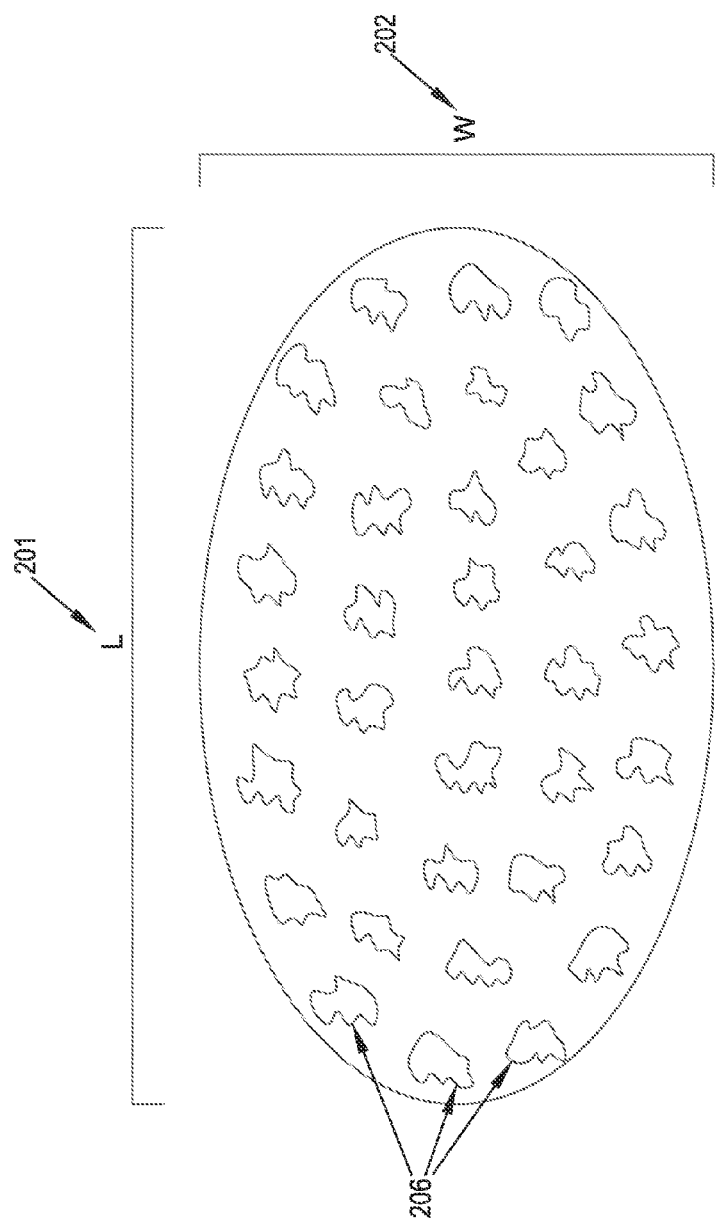

Oval sheet 200 in FIG. 2A has elements 201 and 202 showing the length and width dimensions of the sheet, respectively. Here, width is defined as the largest measurement in the width dimension. In the example embodiment, the length/width ratio will be greater than about 1.6. In an example embodiment, the length of the sheet is in the range of about 12 inches to about 100 inches in length and in the range of about 5 inches to about 24 inches in width, more preferably in the range of about 24 inches to about 72 inches in length and in the range of about 6 inches to about 12 inches in width. In addition, the surface area of the sheet designed to absorb and retain the sunscreen formulation will be greater than about 80 square inches. In another embodiment, the surface area of each side of the sheet designed to absorb and retain the sunscreen formulation will be greater than about 80 square inches.

Figure 3A:
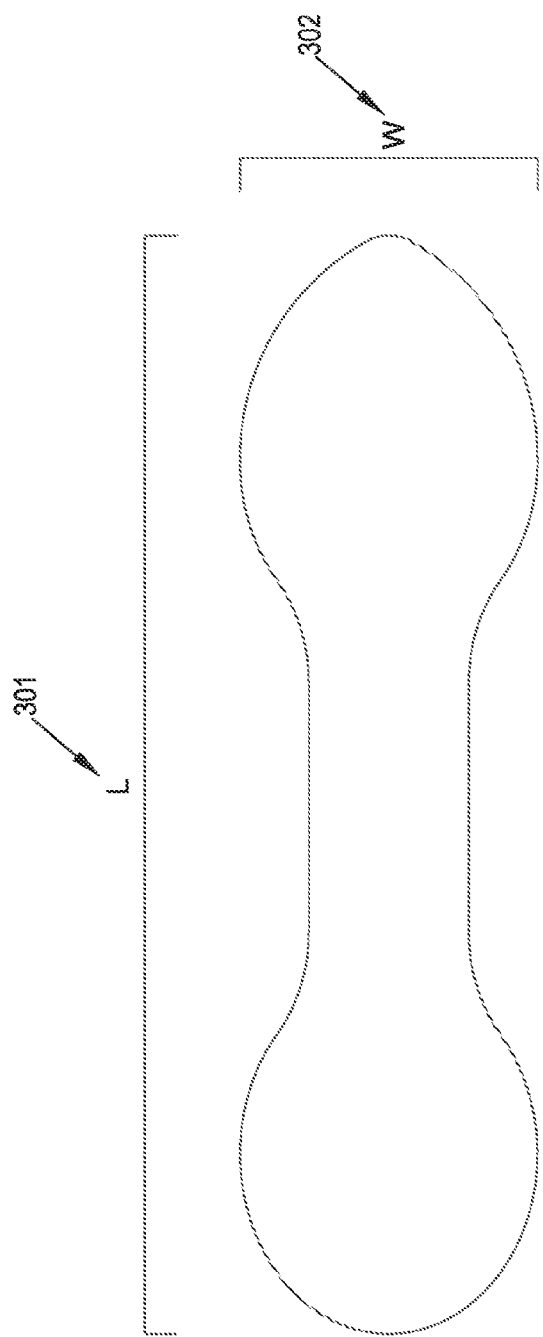
FIG. 3A depicts a top-down view of an hourglass sheet.
Figure 3B:
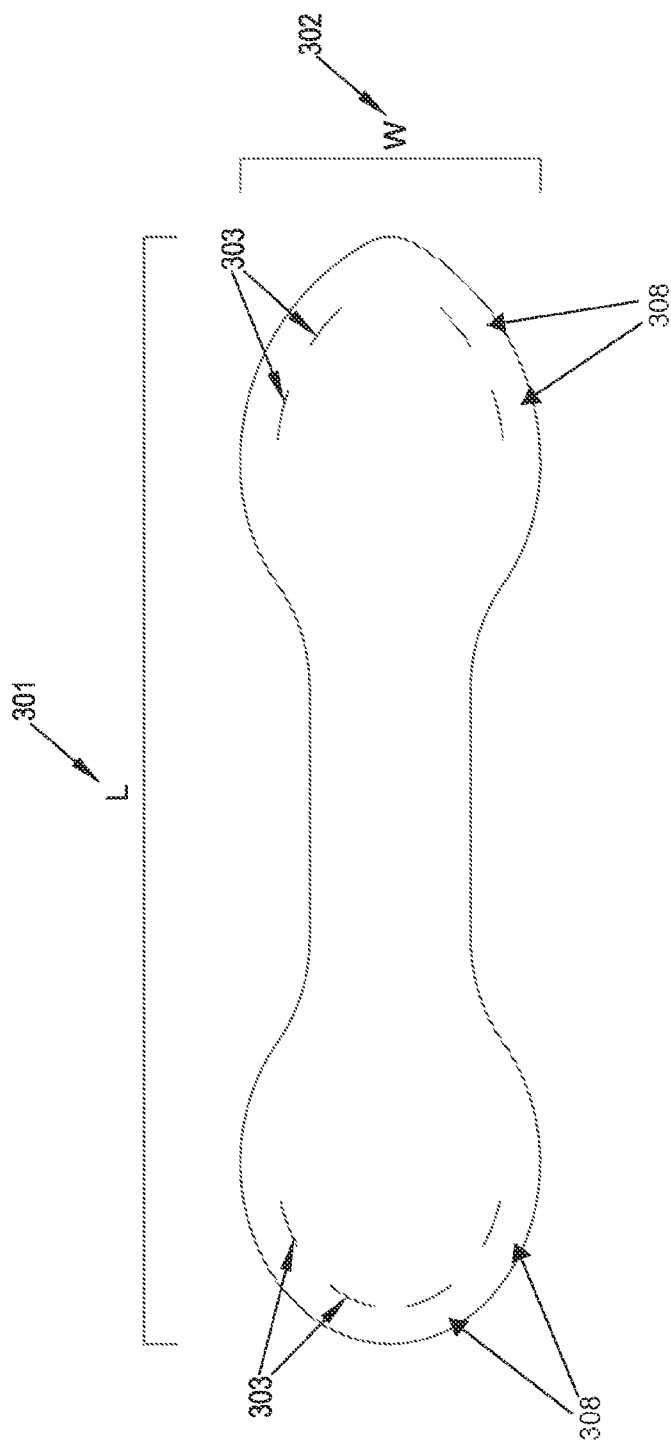
FIGS. 3B, 3C, 3D and 3E depict top-down views of various embodiments in an hourglass sheet.
Figure 3C:
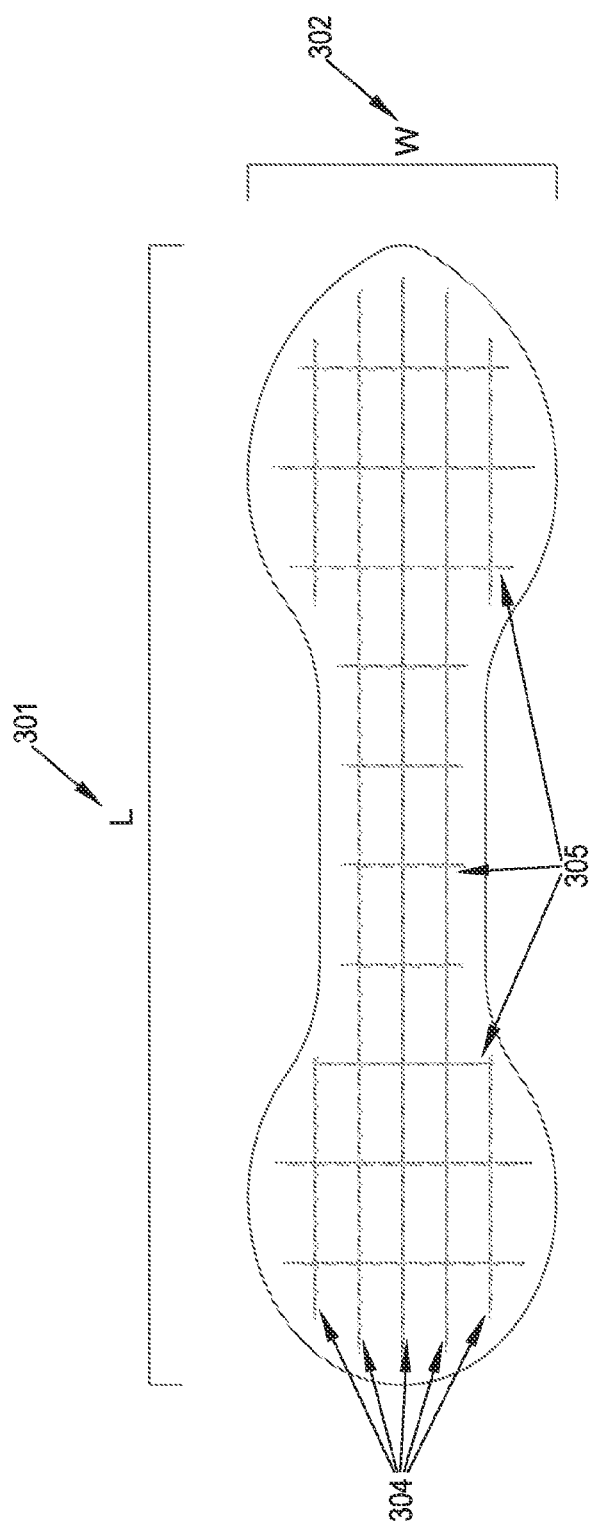
Figure 3D:
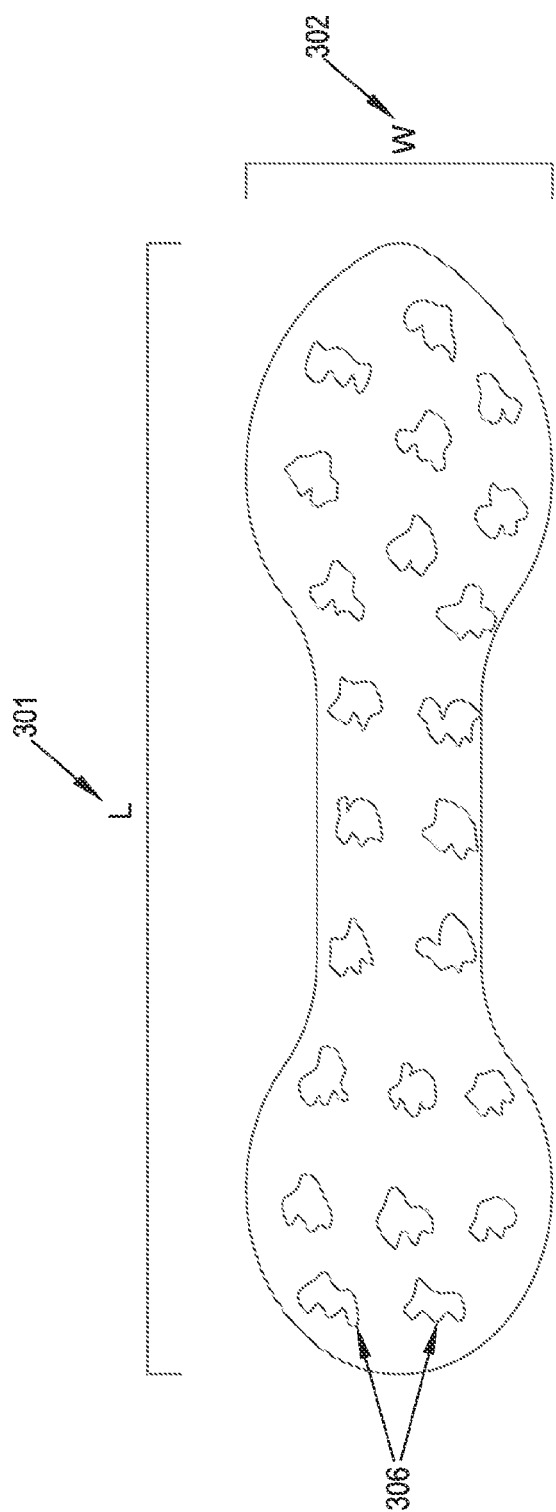

Hourglass sheet 300 in FIG. 3A has elements 301 and 302 showing the length and width dimensions of the sheet, respectively. Here, width is defined as the largest measurement in the width dimension. In the example embodiment, the length/width ratio will be greater than about 1.6. In an example embodiment, the length of the sheet is in the range of about 12 inches to about 100 inches in length and in the range of about 5 inches to about 24 inches in width, more preferably in the range of about 24 inches to about 72 inches in length and in the range of about 6 inches to about 12 inches in width. In addition, the surface area of the sheet designed to absorb and retain the sunscreen formulation will be greater than about 80 square inches. In another embodiment, the surface area of each side of the sheet designed to absorb and retain the sunscreen formulation will be greater than about 80 square inches.

In a specific embodiment of the present disclosure, a user may utilize the impregnated sheet to apply sunscreen to the user's back or entire exposed skin with or without assistance from another person. Consequently, structural modifications such as the addition of hand slits, mitts or finger holes incorporated into the perimeter of the sheet, which enable the user to grasp the sheet, are contemplated. Mitts 103, 203 and 303 are depicted in FIGS. 1B, 2B, 3B and 3F, respectively. Structural modifications may also include or consist of a single or multiple areas that are not impregnated with a sunscreen composition to allow, for example, for holding the sheet during sunscreen application. Non-impregnated area 108, 208 and 308 are depicted in FIGS. 1B, 2B, 3B and 3F, respectively. The non-impregnated area may have a plastic, resin, film or some other material to separate the impregnated area(s) of the sheet versus the non-impregnated area(s) of the sheet.

Woven and non-woven sheets impregnated with a sunscreen composition are often subject to tearing due to the decreased wet strength. Consequently, it is desirable to increase the mechanical strength of the sheet to prevent ripping or tearing during application. The sheet can incorporate structural modifications in order to increase the mechanical strength properties. Non-limiting examples of structural modifications intended to increase the mechanical strength of the sheet useful in the present disclosure are those selected from the group consisting of horizontal stitching, vertical stitching, adhering the sheet to a plastic or rubber structural backing and adhering a plastic or rubber structural backing between two sheet layers. Horizontal stitching 104, 204 and 304 as well as vertical stitching 105, 205 and 305 are depicted in FIGS. 1C, 2C, 3C and 3F, respectively. Adhering a sheet to a structural backing is depicted in FIG. 4A while adhering a structural backing to and between two sheets is depicted in FIG. 4B.

In addition to these structural modifications, other modifications such as adding thermal or chemical binders, including, but not limited to plastics, rubbers or resins can be incorporated into the fabric to increase the mechanical strength of the sheet.

Figure 1E:
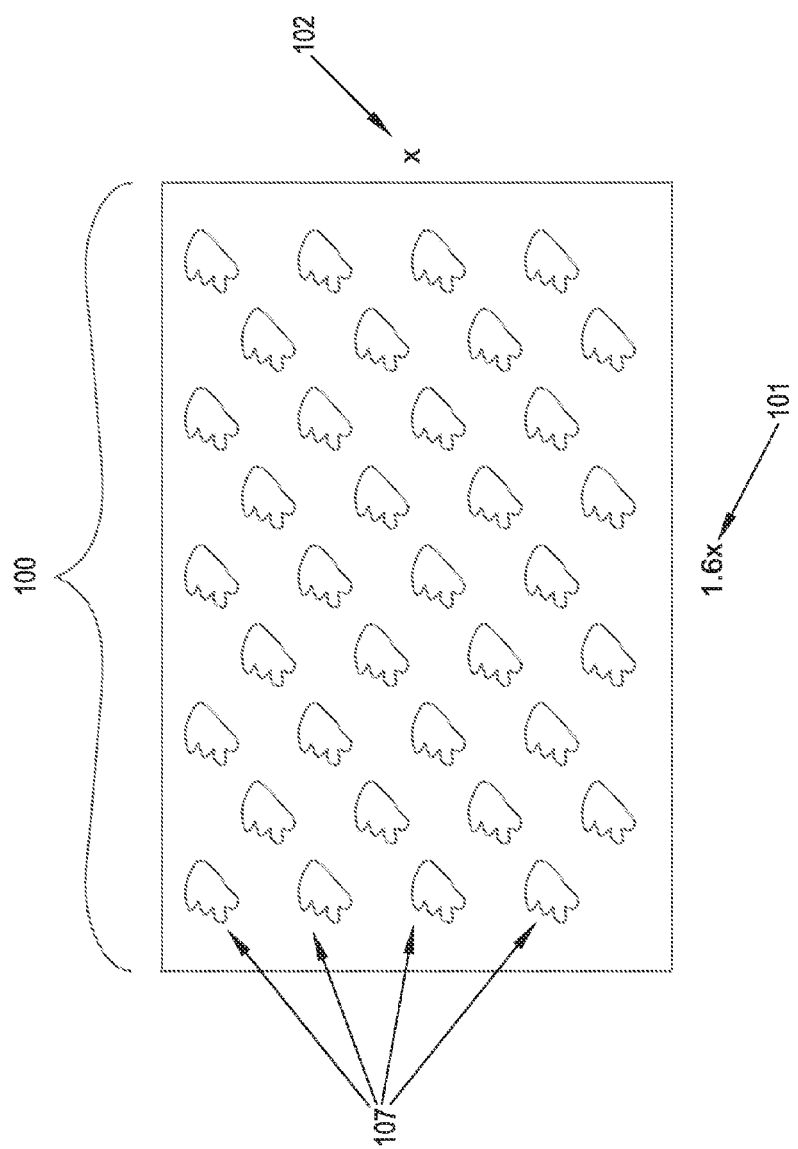
Figure 2E:
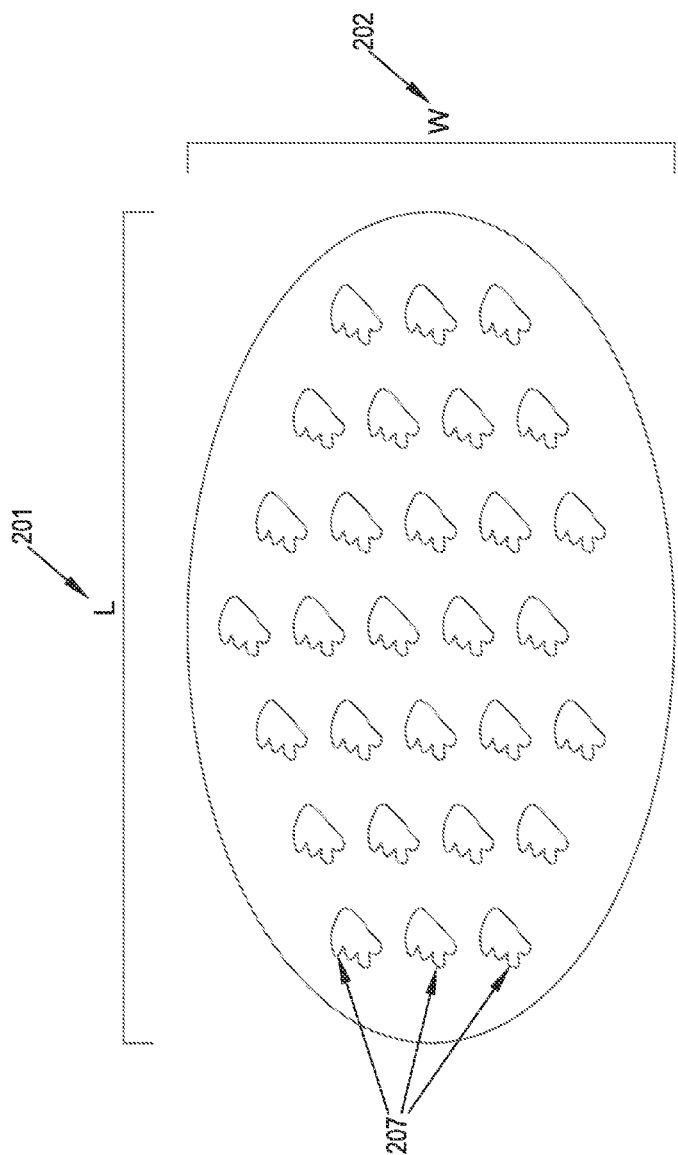
Figure 3E:
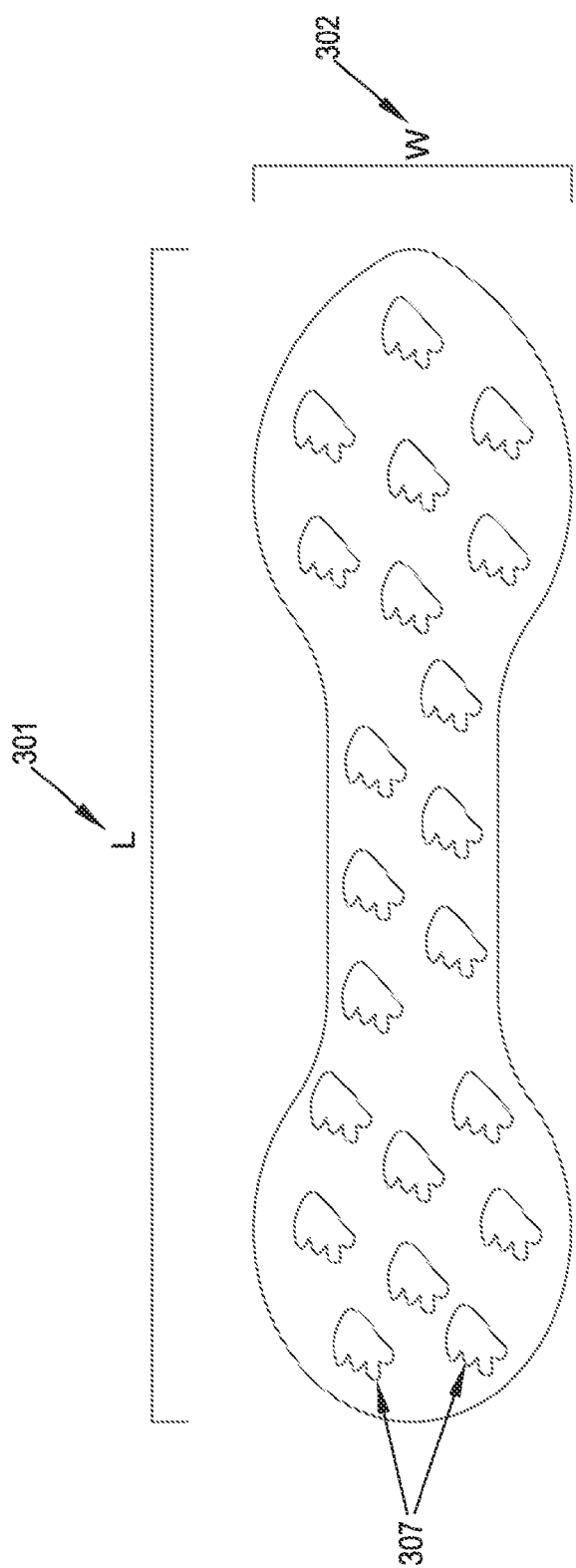

One aspect of the disclosure is to create a sheet which can retain enough sunscreen composition to apply an even coating to an adult or other human's back or entire body, at least one time. Therefore, the addition of quilting or a granulated/textured surface to the sheet is contemplated. FIGS. 1D, 2D, 3D and 3F depict irregular quilting 106, 206 and 306, respectively, added to the surface of the sheet. FIGS. 1E, 2E and 3E depict regular quilting 107, 207 and 307, respectively added to the surface of the sheet.

Figure 3F:
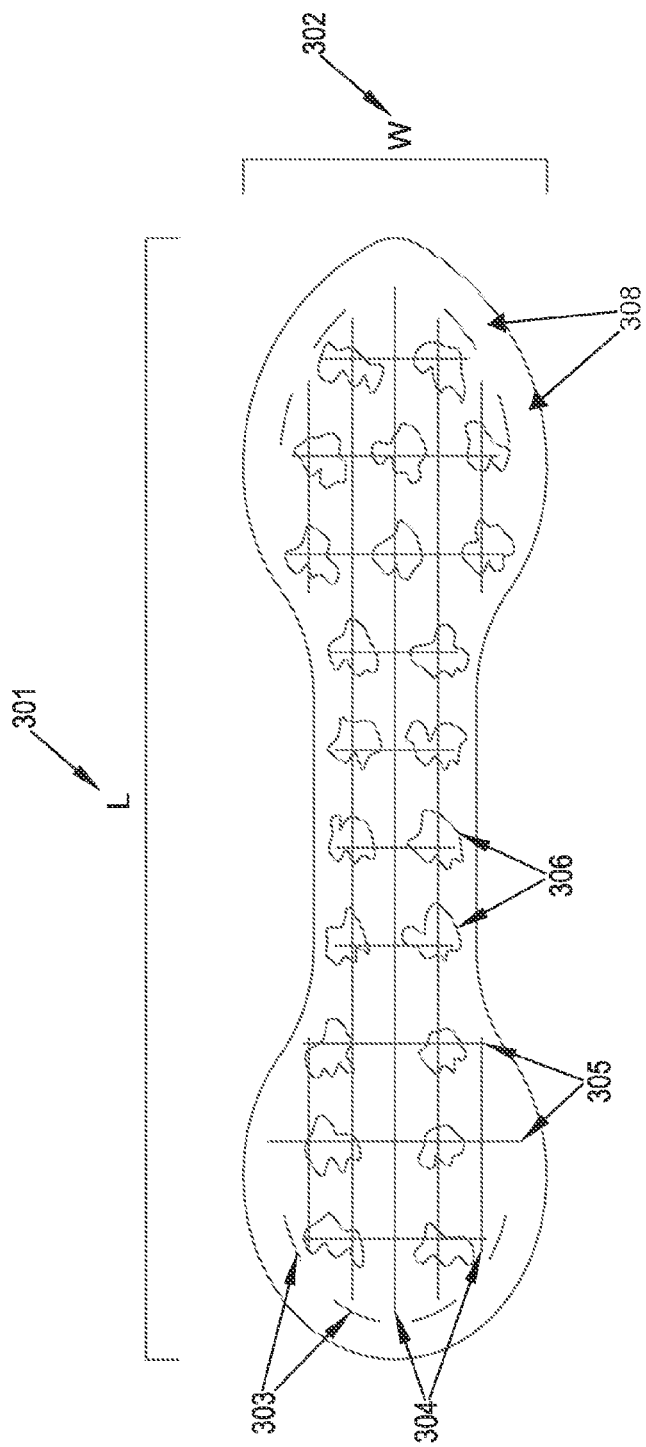
FIG. 3F depicts a top-down view of all the embodiments depicted in FIGS. 3B, 3C and 3D.
Figure 4A:
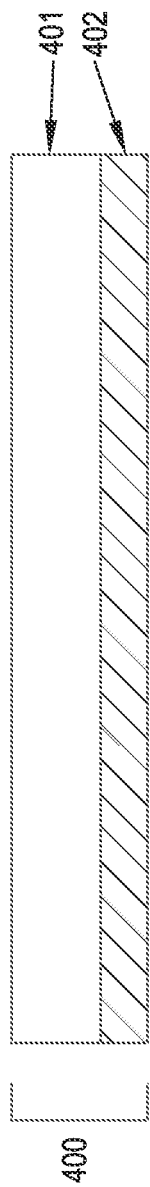
FIG. 4A depicts a sheet adhered to a structural backing.
Figure 4B:
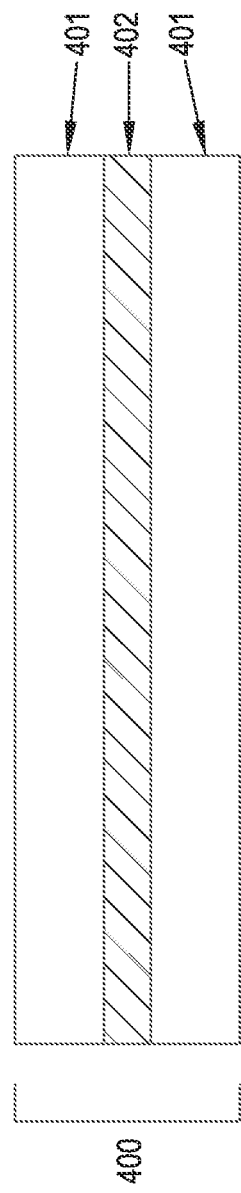
FIG. 4B depicts a structural backing adhered to and sandwiched between two sheets.

As an illustrative and non-limiting example of the present disclosure, mitts 303, horizontal stitching 304, vertical stitching 305 and irregular quilting 306 are depicted on an hourglass sheet in FIG. 3F. It should be apparent to one of ordinary skill in the art that any combination of these embodiments and others can be employed on any shaped sheet. It should also be apparent to one of ordinary skill in the art that any combination of these embodiments and others can be applied to sheets adhered to structural backing The sunscreen composition will be formulated to be sufficiently fluid to allow absorption and retention in the sheet. Non-limiting formulations useful in the present disclosure may be selected from the group consisting of oils, gels, creams, lotions, liquids and others. Furthermore, the composition will be released from the sheet upon gentle rubbing over the user's skin and will, preferable, form a thin, non-greasy and non-tacky film over the user's skin.

UV blocking agents are well known in the art. Broad-spectrum sunscreens are able to block both UV-A and UV-B radiation, corresponding to wavelengths between about 280 nm to about 400 nm. It is also well known that UV blacking agents are made of either organic molecules which absorb UV radiation or inorganic particles which reflect or scatter UV radiation. Additionally, there is a newer class of organic molecule particulates which both absorb and scatter UV radiation. Non-limiting agents useful in the present disclosure will be selected from the group consisting of amiloxate, avobenzone, bemotrizinol, bisoctrizole, cinoxate, dioxybenzone, drometrizole trisiloxane, ecamsule, enzacamene, homosalate, iscotrizinol, menthyl anthranilate, octinoxate, octocrylene, octyl methoxycinnamate, octyl salicylate, octyl triazone, oxybenzone, padimate O, para-aminobenzoic acid, phenylbenzimidazole sulfonic acid, sulisobenzone, trolamine salicylate, titanium dioxide and zinc oxide or other UB blocking agents.

Additional UV blocking agents useful in the present disclosure may be selected from the group consisting of benzophenone-9, 4-methylbenzylidene camphor, isopentenyl-4-methoxycinnamate, Mexoryl XL, Neo Heliopan AP, Parsol SLX, Tinosorb M, Tinosorb S, Uvasorb HEB, Uvinul A Plus and Uvinul T 150 or other UV blocking agents.

In order to reduce the viscosity of the sunscreen formulation, a solvent system often consisting of water and/or alcohol is often used. If the alcohol content is too high, the sunscreen may cause an unwanted burning sensation and/or drying of the user's skin. If the water content is too high, emulsification of the hydrophobic blocking agents is often difficult to achieve. Thus, the sunscreen formulation will be balanced such that the viscosity is low enough to allow uptake and absorption of the formulation into the sheet while the hydrophobic blocking agents are emulsified and distributed in the solvent system Due to the fact that the blocking agents are often hydrophobic and insoluble in water, a surfactant or emulsifier system is also incorporated into the formulation to disperse the blocking agents in the solvent system. Non-limiting surfactants or emulsifiers useful in the present disclosure can be selected from the group consisting of anionic surfactants, cationic surfactants, nonionic surfactants, amphoteric surfactants and others.

In addition, emollients and other inactive compounds are often used in sunscreen formulations to moisten the user's skin and provide other benefits. Non-limiting inactive compounds useful in the present disclosure can be selected from the group consisting of hydrocarbons, silicones, fatty alcohols, synthetic esters, natural esters, Vitamin A, Vitamin B, and Vitamin C as well as herbal and botanical extracts.

It should be recognized by one of ordinary skill in the art that the sheets described herein may be used to apply other compositions besides sunscreen. Non-limiting examples of other compositions capable of being applied with a sheet set forth in this description can be selected from the group consisting of moisturizing compositions, anti-aging compositions, insect repellent compositions, anti-bacterial compositions, anti-inflammatory compositions, anti-fungal compositions, sun burn treatment compositions, makeup compositions, dermatological compositions, pharmaceutical compositions, medical compositions, and others.

Having described at least one of the example embodiments of the present disclosure with reference to the accompanying drawings, it is to be understood that the disclosure is not limited to those precise embodiments, and that various changes, modifications, and adaptations may be effected therein by one skilled in the art without departing from the scope or spirit of the disclosure as defined in the appended claims.

ILLUSTRATIVE EXAMPLE

Sheet fabrics that were selected were sourced from Lymtech. The fabrics selected were C30, C30L, G7, and XL7400. C30 and C30L have a polyester/cellulose composition; G7 has a cotton composition and XL7400 has a hydroentagled rayon composition. The C30 fabric comprises a basis weight of 2.0 ounces per yard squared and a thickness of 12 mils. The C30L fabric comprises a basis weight of 1.6 ounces per yard squared and a thickness of 9 mils. The G7 fabric comprises a basis weight of 1.7 ounces per yard squared and a thickness of 11 mils. The XL7400 fabric comprises a basis weight of 2.0 ounces per yard squared and a thickness of 17 mils. Three different types of sunscreen products were tested for chemical compatibility with these fabrics: Badger Sport SPF 35 (LL0133), Kabana SPF 35 (LL0134), and CVS 50 Baby Sun Lotion (LL01414). Based on a physical examination and strength test of the exposed fabric, all four types of fabrics were compatible with all three sunscreen products with no discernible effects on the fabrics stability.

Chemical compatibility testing was done based on a physical examination and strength test of the fabrics prior to application of the sunscreen and then after the sunscreen had been applied and conditioned for 72 hours. The fabric pieces tested were cut into 9"×2" strips. The sunscreen was applied in a 2"×2" square on the lower end of the fabric leaving space for clamps to be attached for strength testing.

The physical examination was done by having a scientist observe the product before and after application of the sunscreen and record any discoloration and/or physical break down of the material. The strength test on the fabric was performed by attaching 10 lbs of weight to the fabric and allowing the weight to pull on the fabric across the 9" length for 2 minutes. Test results were compared for each fabric/sunscreen combination to the results from the as received fabrics. No discernible differences were observed between the fabrics as received and the fabrics after sunscreen had been applied. It was observed that the lower viscosity sunscreen, LO1414, had a larger amount of solvent wicking over the fabric strips than the more viscous samples, LO1333 and LO1334.

Based on the results of this testing, it was concluded that there was no interaction between the sunscreen and the fabrics in regards to the fabric's stability. Therefore, all fabrics and sunscreens were deemed compatible. Based on the texture and physical properties of the fabrics, G7 and XL7400 were selected for further product development.

Prototypes were developed after assessment of the fabric/sunscreen interactions based on the physical properties of the individual fabrics. From the testing outlined above, the fabrics that proved to be most durable and applicable to the nature of the product were XL7400 and G7. These two fabrics were tested for the ability to absorb and then apply the selected sunscreens to human skin. In one example, the applications of the sunscreen in terms of mass of sunscreen applied to the skin per square inch of fabric were found to be utilizing LO1334 and LO1414. Based on these results, example prototypes were developed in a 60"×7" sheet with a 48"×7" coated area using the two identified sunscreens and the two identified fabrics for a total of 4 prototypes.

In an effort to assess the amount of sunscreen absorbed by the fabric and the amount of sunscreen that could be applied from the soaked fabric to human skin, a study was designed to measure these values. 9"×9" pieces of fabric were coated with the identified sunscreens, LO1334 and LO1333, using a 7" wide draw down bar. The height of the bar was set using the calipers to 15 mm for the initial coating. Once the fabrics were fully coated, the height was step-wise adjusted down to a final height of 5 mm and the coating was spread as thin as possible to minimize the coating thickness. The sample fabrics were weighed before application of the sunscreen, after applying the sunscreen, and then after the coated fabrics were applied to human skin. Calculations for measuring the applications were performed as follows:

Weight of Sunscreen Absorbed=Weight of Sunscreen Coated Cloth−Weight of Cloth (Before Coating)

Weight of Sunscreen Applied=Weight of Sunscreen Coated Cloth−Weight of Coated Cloth After Application to Skin Calculations for the amount of sunscreen absorbed and applied per square inch of fabric were performed using the 9"×7" area that was coated with the sunscreen, even though there was extra uncoated area on the fabric. These values were then scaled-up assuming a final coated sheet dimension of 48"×7". The calculations found that neither LO1333 nor LO1334 were estimated to supply the identified amount of 40 grams of sunscreen on either fabric. Based on the calculations (summarized in Table 2) found for LO1333 and LO1334, LO1414 was tested on the XL7400 fabric in order to assess its viability as another possible sunscreen. Calculations for LO1414 identified that over 40 grams of sunscreen could be applied from the coated fabric. Table 2 summarizes the results for all of the material testing. The LO1414 and LO1334 were identified as possible options for implementation of the sheet material based on amounts applied from the fabric onto the skin. In a specific embodiment, the XL7400 fabric was selected as the sheet material for absorption and application of the sunscreen composition.

TABLE 2

| Sunscreen | Fabric | Wt of Sunscreen Absorbed 9" × 7" | Wt of Sunscreen Applied 9" × 7" | Estimated Wt of Sunscreen Applied for 48" × 7" |
|---|---|---|---|---|
| LO1333 | XL7400 | 10.338 | 0.6864 | 3.203 |
| LO1333 | G7 | 6.0451 | 0.2875 | 1.3417 |
| LO1334 | XL7400 | 14.6759 | 3.0693 | 14.3232 |
| LO1334 | G7 | 9.2887 | 1.7934 | 8.3690 |
| LO1414 | XL7400 | 24.6319 | 9.1346 | 42.6279 |

What is claimed is:

1. A dermatological sheet for use in the application of a sunscreen composition comprising:
a water-insoluble quilted sheet having a surface area greater than about 80 square inches on said water-insoluble quilted sheet and said water-insoluble quilted sheet having a length to width ratio of greater than about 1.6 to 1, said water-insoluble quilted sheet having a basis weight of at least 1.6 ounces per square yard and a thickness of at least 9 mils, said water-insoluble quilted sheet having an untreated tensile strength of at least 15.5 lbs perpendicular to a grain of said water-insoluble quilted sheet, and
a sunscreen composition,
wherein said water-insoluble quilted sheet is impregnated with said sunscreen composition, wherein said water-insoluble quilted sheet is sized sufficiently to facilitate a user to apply an even application of said sunscreen composition to a back of said user, said tensile strength sufficient to prevent tearing of said water-insoluble quilted sheet during application of said sunscreen composition to said back of said user.

2. The dermatological sheet of claim 1:
wherein said water-insoluble quilted sheet comprises woven or non-woven fibrous material.

3. The dermatological sheet of claim 2:
wherein said water-insoluble quilted sheet comprises spandex fibers, lycra fibers, neoprene fibers, elastane fibers, rayon fibers or combination thereof.

4. The dermatological sheet of claim 3:
wherein said water-insoluble quilted sheet comprises a hydroentangled cotton composition.

5. The dermatological sheet of claim 2:
wherein said water-insoluble quilted sheet comprising a basis weight of at least 1.6 ounces per square yard and a thickness of at least 9 mils.

6. The dermatological sheet of claim 1 further comprising:
at least one area of the water-insoluble quilted sheet that is not impregnated with the sunscreen composition.

7. The dermatological sheet of claim 6:
wherein the at least one area of the water-insoluble quilted sheet comprises plastic, resin, or film.

8. The dermatological sheet of claim 1 further comprising:
dye, paint, tint or emboss.

9. The dermatological sheet of claim 1 further comprising:
mitts, hand slits or finger holes.

10. The dermatological sheet of claim 1 further comprising:
stitching.

11. The dermatological sheet of claim 1:
wherein the water-insoluble quilted sheet is in the shape of an hourglass, rectangle or oval.

12. The dermatological sheet of claim 1:
wherein the water-insoluble quilted sheet has a length between about 30 inches and about 80 inches and a width between about 6 inches and about 10 inches.

13. The dermatological sheet of claim 1:
wherein the sunscreen composition is in an amount greater than or equal to about 2 mg of sunscreen composition to apply sunscreen to the human user's back or entire body.

14. A dermatological sheet for use in the application of a sunscreen composition comprising:
a water-insoluble quilted sheet having a length to width ratio of greater than about 1.6 to 1, the water-insoluble quilted sheet having a basis weight of at least 1.6 ounces per square yard and a thickness of at least 9 mils, the water-insoluble quilted sheet having a tensile strength of 15.5 lbs perpendicular to a grain of the water-insoluble quilted sheet;

a sunscreen composition, the water-insoluble quilted sheet impregnated with the sunscreen composition over an area greater than about 80 square inches;

wherein the water-insoluble quilted sheet has a surface area sufficient to facilitate an even application of the sunscreen composition by the user to the back of the user by dragging the water-insoluble quilted sheet over the back of the user, the tensile strength sufficient to prevent tearing of the water-insoluble quilted sheet during application of the sunscreen composition to the back of the user.

15. The dermatological sheet of claim 14, further comprising:

a structural backing adhered to the water-insoluble quilted sheet, the structural backing configured to increase a mechanical strength of the water-insoluble quilted sheet.

16. The dermatological sheet of claim 14, further comprising:

wherein the length to width ratio comprises a range between about 4 to 1 and about 12 to 1.

17. The dermatological sheet of claim 14, wherein the sunscreen composition is in an amount greater than or equal to about 2 mg of sunscreen composition to apply sunscreen to the human user's back or entire body.

18. A dermatological sheet for use in the application of a sunscreen composition comprising:

a water-insoluble quilted sheet having a surface area greater than about 80 square inches on said water-insoluble quilted sheet and said water-insoluble quilted sheet having a length to width ratio greater than 1.6 to 1, said water-insoluble quilted sheet having a basis weight of at least 1.7 ounces per square yard and a thickness of at least 11 mils, said water-insoluble quilted sheet having a tensile strength of 15.7 lbs perpendicular to a grain of said water-insoluble quilted sheet, and a sunscreen composition, wherein said water-insoluble quilted sheet is impregnated with said sunscreen composition, and wherein said water-insoluble quilted sheet is sized sufficiently to facilitate a user to apply an even application of said sunscreen composition to cover all or part of said body of said user, said tensile strength sufficient to prevent tearing of said water-insoluble quilted sheet during application of the sunscreen composition to said back of said user.

19. The dermatological sheet of claim 18, further comprising:

a structural backing adhered to said water-insoluble quilted sheet, the structural backing configured to increase a mechanical strength of said water-insoluble quilted sheet.

20. The dermatological sheet of claim 14, wherein said water-insoluble quilted sheet has a length ranging from about 24 inches to about 72 inches and a width ranging from about 3 inches to about 6 inches.

* * * * *